United States Patent [19]

Morris et al.

[11] Patent Number: 5,596,020

[45] Date of Patent: Jan. 21, 1997

[54] AMINO BI- AND TRI-CARBOCYCLIC ALKANE BIS-ARYL SQUALENE SYNTHASE INHIBITORS

[75] Inventors: Robert L. Morris, Wayne; Kent W. Neuenschwander, Schwenksville; Keith S. Learn, Perkiomenville; Anthony C. Scotese, King of Prussia, all of Pa.

[73] Assignee: Rhone-Poulenc Rorer Pharmaceuticals Inc., Collegeville, Pa.

[21] Appl. No.: 350,593

[22] Filed: Dec. 7, 1994

Related U.S. Application Data

[62] Division of Ser. No. 83,117, Jun. 25, 1993, Pat. No. 5,395,846.

[51] Int. Cl.$^6$ ........................................... A61K 31/135
[52] U.S. Cl. ..................... 514/646; 514/650; 514/656; 514/662; 564/384; 564/427; 564/443; 564/459
[58] Field of Search ................................. 564/427, 428, 564/443, 384, 459; 514/646, 656, 657, 650, 662

[56] References Cited

U.S. PATENT DOCUMENTS 4,100,170   7/1978   Shetty ..................................... 564/427

Primary Examiner—Brian M. Burn
Attorney, Agent, or Firm—James A. Nicholson; Martin F. Savitzky; Raymond S. Parker, III

[57] ABSTRACT

This invention relates to a class of novel amino bi- and tri-carbocyclic alkane compounds having bis-aryl substitution which exhibit squalene synthase inhibition properties. The bi- and tri-carbocyclic alkane ring contains an amino group and the ring is further linked or bridged to two mono- and/or bicyclic rings. Compounds of this invention reduce levels of serum cholesterol in the body without significantly reducing mevalonic metabolite synthesis. This invention relates also to pharmacological compositions and method of treatment for lowering serum cholesterol levels using the compounds of this invention.

12 Claims, 1 Drawing Sheet

Figure 1

AMINO BI- AND TRI-CARBOCYCLIC ALKANE BIS-ARYL SQUALENE SYNTHASE INHIBITORS

This is a divisional of application Ser. No. 08/083,117 filed on Jun. 25, 1993 (now U.S. Pat. No. 5,395,846).

FIELD OF THE INVENTION

The present invention relates to a class of novel compounds useful in the treatment of diseases associated with undesirable cholesterol levels in the body, and particularly diseases of the cardiovascular system, such as atherosclerosis.

Figure 1:
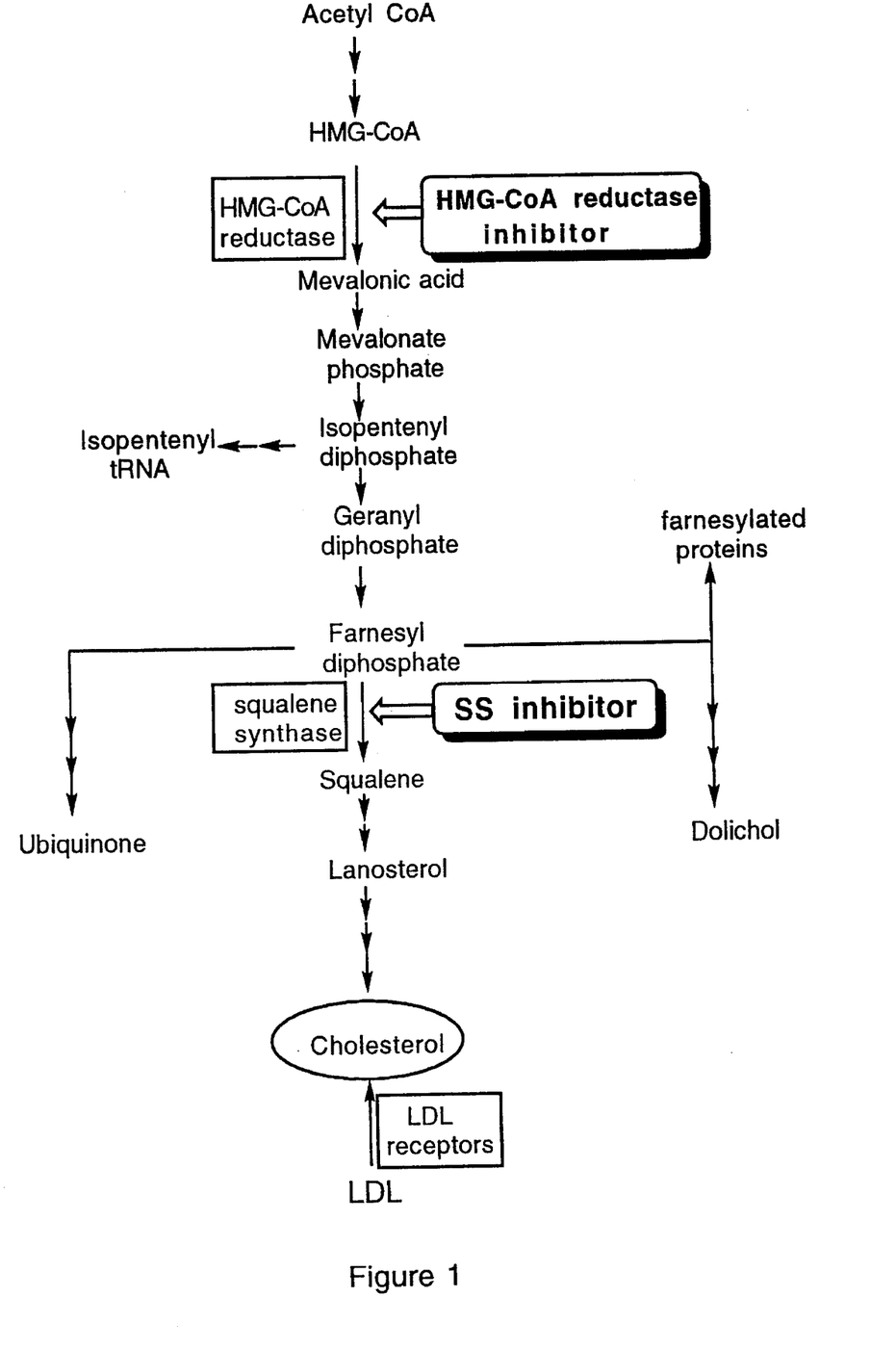
FIG. 1 is a schematic diagram of the biosynthetic pathway of cholesterol.

Only about 7% of the total body cholesterol circulates in the plasma, where it has been linked to atherosclerosis. The remaining 93% is located in cells, where it performs vital structural and metabolic functions. Excluding the diet, which accounts for approximately one-third of the total body cholesterol, the cells obtain the necessary cholesterol by endogenous biosynthesis (FIG. 1) or by removing low density lipoprotein (LDL) from the bloodstream. Approaches to the control of plasma cholesterol levels have been varied, however it has been shown that inhibiting endogenous cholesterol biosynthesis forces the cell to rely more on LDL uptake to satisfy their cholesterol requirements. Increased LDL uptake by cells, especially liver cells, has been shown to lower plasma cholesterol levels.

Squalene synthase is a microsomal enzyme that catalyzes the reductive dimerization of two molecules of farnesyl diphosphate to form squalene. While farnesyl diphosphate serves as the precursor to several other biologically important compounds, squalene is utilized only for cholesterol biosynthesis. Consequently, this is the first totally committed step in the biosynthesis of cholesterol (see FIG. 1). Inhibition at this step would stop only de novo cholesterol synthesis while allowing other essential pathways to isopentenyl tRNA, the prenylated proteins, ubiquinone, and dolichol to proceed unimpeded.

Inhibition of HMG-CoA reductase, an enzyme positioned early in the cholesterol biosynthetic pathway, results in a decrease of de novo cholesterol biosynthesis and an accompanying up-regulation of LDL receptors. However due to a large induction in the amount of the HMG-CoA reductase enzyme, the effect of this inhibition is blunted somewhat and the maximum LDL cholesterol reductions attainable are limited. Since inhibition of squalene synthase does not cause the same amount of enzyme induction (HMG-CoA reductase or squalene synthase), its inhibition results in a greater reduction of de novo cholesterol biosynthesis. This translates into more up-regulation of LDL receptors than is seen with an HMG-CoA reductase inhibitor and greater efficacy for lowering circulating LDL levels.

Reported Developments

The literature describes the cholesterol biosynthetic pathway and possible means for the inhibition of squalene synthase. In a series of papers including *J. Am. Chem. Soc.*, 1982, 104, 7376–7378 and *J. Am. Chem. Soc.*, 1989, 111, 3734–3739, C. Dale Poulter, et al disclose that ammonium substituted cyclopropyl polyene compounds mimic the topological and electrostatic properties of the primary cation and tertiary cation of presqualene diphosphate, and in the presence of phosphate buffer, inhibit squalene synthase, Scott A. Biller et al in *J. Med. Chem.*, 1988, 31, 1869–1871 disclose that a series of stable, non-ionizable analogues of farnesyl diphosphate, comprising phosphomethylene phosphate polyene compounds, inhibit squalene synthase.

Paul E. Schurr and Charles E. Day in *Lipids*, Vol. 12, No. 1, 22–28 describe a compound known as U-41,792, 1-[p-(1-adamantyloxy)phenyl]piperidine, which is stated to cause a reduction in lower density lipoproteins, and is designated by the authors as having hypobetalipoproteinemia activity International Patent Application published under the Patent Cooperation Treaty having International Publication Number: WO 92/15579 is directed to multicyclic tertiary amine polyaromatic squalene synthase inhibitors containing a multiazacyclic ring; U.S. Ser. No. 07/997,818, filed Dec. 29, 1992 (now U.S. Pat. No. 5,451,596) is directed to cycloalkyl amine bis-aryl squalene synthase inhibitors; and U.S. Ser. No. 08/65,966 filed May 21, 1993 (now U.S. Pat. No. 5,455,260) is directed to aliphatic amino bis-aryl squalene synthase inhibitors. Each is assigned to the same assignee as the present application. These applications are not directed to bi- or tri-carbocycloalkane compounds as disclosed in the present invention.

U.S. Pat. No. 5,135,935 assigned to Merck and Co., is directed to squalene synthase inhibitors which are aryloxadiazole-quinuclidines. International Patent Applications published under the Patent Cooperation Treaty having International Publication Numbers: WO 92/12159, 92/12158, 92/12157, 92/12156 and 92/12160 and being assigned to Glaxo Group Ltd. are directed to bridged cyclic ketal derivatives for lowering the level of blood plasma cholesterol.

The present invention is directed to a class of novel amino bi- and tri-carbocyclic alkane compounds having bis-aryl substitution which exhibit squalene synthase inhibition properties.

SUMMARY OF THE INVENTION

This invention comprises compounds which are bi- and tri-carbocyclic alkane compounds substituted with an amino group and which is further bridged to two mono- and/or bicyclic aryl and/or heteroaryl rings. The compounds of this invention possess properties which reduce levels of serum cholesterol in the body without significantly reducing mevalonic metabolite synthesis and thus provide a therapeutic agent having fewer side effects than agents which act by inhibiting the HMG-CoA reductase enzyme. This invention relates also to pharmacological compositions and method of treatment for lowering serum cholesterol levels using the compounds of this invention.

More specifically, the compounds of this invention are described by the compounds of Formula I:

where:

A is O, S, NR, SO, $SO_2$, O=C, NR—C=O, O=C—NR, RC=CR, C≡C or a bond;

B is $(CR_2)_e$, O, S, NR, SO, $SO_2$, NR—C=O, O=C—NR, RC=CR, C≡C, O=C or a bond;

R is hydrogen or alkyl;

R' is hydrogen, alkyl or acyl;

R" is hydrogen or alkyl;

$R_1$ and $R_2$ are independently hydrogen, alkyl, alkoxy, hydroxy, halo, haloalkyl, nitro, amino, mono- or di-alkylamino or phenyl;

$R_3$ is hydrogen, alkyl, hydroxy, alkoxy, acyloxy, amino, mono- or di-alkylamino, acylamino, halo or haloalkyl;

$R_4$ is hydrogen, alkyl, hydroxy, alkoxy, acyloxy, acylamino, halo or haloalkyl;

Alk is bi- or tri-carbocycloalkane;

Ar I and Ar II are aryl;

a and b are independently 0–3;

a+b is 0–3;

d is 0–3 e is 1–3;

m and n are 0–2; and its stereoisomers, enantiomers, diastereoisomers and racemic mixtures; or a pharmaceutically acceptable salt thereof.

DETAILED DESCRIPTION AND PREFERRED EMBODIMENTS

As employed above and throughout this disclosure, the following terms, unless otherwise indicated, shall be understood to have the following meanings:

"Acyl" means a organic radical derived from an organic acid by the removal of its hydroxyl group. Preferred acyl groups are lower alkanoyl groups having 1 to about 6 carbon atoms. Most preferred lower alkanoyl are acetyl and propionyl.

"Alkyl" means a saturated aliphatic hydrocarbon, either branched- or straight-chained. Preferred alkyl is "lower-alkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group.

"Aryl" means a monocylic or bicyclic carbocyclic or heterocyclic aromatic ring.

"Bi-carbocyclic alkane ring" is a ring system composed of two fused carbocyclic rings. Preferred bi-carbocyclic alkane rings include bicyclo[2.2.1]heptane, bicyclo[2,2,2]octane, bicyclo[3.2.1]octane, bicyclo[3.2.2]nonane, bicyclo[3.3.1]nonane, bicyclo[4.2.1]nonane and bicyclo[2.2.2]octene.

"Bicyclic aryl" means a bicyclic ring system composed of two fused carbocyclic and/or heterocyclic aromatic rings. Preferred bicyclic rings include substituted and unsubstituted indene, isoindene, benzofuran, dihydrobenzofuran, benzothiophene, indole, 1H-indazole, indoline, azulene, tetrahydroazulene, benzofuran, benzothiaphene, benzopyrazole, benzoimidazole, benzoxazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benzisoxazine. Most preferred groups include naphthyl, benzoxazolyl, indolyl, benzothienyl, benzofuranyl, quinolinyl and benzothiazole.

"Biological pH" refers to that pH of blood, plasma or serum in the body between about 7.2 and about 7.5 and which does not interfere with normal degradation of materials present therein. The normal pH of blood, plasma or serum values is about 7.35–7.45 and is preferably about pH 7.39–7.41.

"Halo" means a halogen. Preferred halogens include chloride, bromide and fluoride. The preferred haloalkyl group is trifluoromethyl.

"Monocyclic aryl" means a monocylic carbocyclic and/or heterocyclic aromatic ring. Preferred rings are substituted or unsubstituted pyrrole, thiophene, furan, imidazole, pyrazole, 1,2,4-triazole, pyridine, pyrazine, pyrimidine, pyridazine, thiazole, isothiazole, oxazole, isoxazole, s-triazine and benzene. Most preferred groups include phenyl, thienyl, pyridinyl, furyl and pyrimidinyl.

"Tri-carbocyclic alkane ring" is a ring system composed of three fused carbocyclic rings. Preferred tri-carbocyclic alkane rings include tricyclo[3.3.1.1$^{3,7}$]decane, tricyclo[2.2.2.2$^{1,4}$]decane, tricyclo[3.2.2.1$^{1,4}$]decane and tricyclo[4.3.1.1$^{3,8}$]decane.

Preferably, Alk is bicyclo[2.2.2]octane or tricyclo[3.3.1.1$^{3,7}$]decane.

Preferably, Ar I and Ar II are independently a substituted or unsubstituted mono- or bicyclic aryl of about 5 to about 12 atoms. At least one ring of these systems is aromatic and the second ring of a bicyclic system may be partially or completely unsaturated carbocyclic or heterocyclic and where each ring of said system contains 0 to about 2 hetero atoms selected from N, O and S provided said hetero atoms are not vicinal oxygen and/or sulfur atoms and where the substituents may be located at any appropriate position of the ring system and are described by the R definition above.

The preferred compounds of this invention include those compounds of Formulae II to V:

Formula II

Formula III

Formula IV

Formula V

More preferred compounds are those of Formulae II to V where:

A is O, S, NR, HC=CH or a bond;

B is $(CR_2)_e$, O, S, NR, HC=CH, O=C or a bond;

R is hydrogen or lower alkyl;

R' is hydrogen, loweralky, acetyl or propionyl;

R" is hydrogen or loweralkyl;

$R_1$ and $R_2$ are independently hydrogen, loweralkyl, loweralkoxy, hydroxy, halo or haloloweralkyl;

$R_3$ is hydrogen, loweralkyl, hydroxy, loweralkoxy, amino, mono- or di-alkylamino or halo;

a and b are independently 0–3;

a+b is 0–3;

d is 0–3;

e is 1–3; and m and n are independently 0–2.

The most preferred compounds are those described by Formulae VI to IX:

Formula VI

Formula VII

-continued

Formula VIII

Formula IX where:
A is O or a bond;
B is HC=CH, O=C or a bond;
R is hydrogen or methyl;
R' is hydrogen, methyl, acetyl or propionyl;
$R_1$ and $R_2$ are independently hydrogen, methyl, ethyl, methoxy, ethoxy, hydroxy, chloro, bromo, fluoro or trifluoromethyl;
$R_3$ is hydrogen, loweralkyl, hydroxy, loweralkoxy, amino, mono- or di-alkylamino or halo;
a and b are independently 0–3;
a+b is 0–3;
e is 1–3; and
m and n are independently 0–2.

A special embodiment of this invention is described by the compounds of Formulae X and XI.

Formula X

Formula XI

The compounds of this invention may be prepared by employing procedures known in the literature starting from known compounds or readily preparable intermediates. Exemplary general procedures follow. These general procedures are shown with the carbocyclic alkane ring as being the tricyclo[3.3.1.1$^{3,7}$] moiety. It is to be understood that this ring is used in the following description to illustrate the invention with representative procedures and examples and not to be considered as limiting the invention to the tricyclo [3.3.1.1$^{3,7}$] ring.

Thus, in order to prepare those compounds where A, B or D is O, S or NR the following reactions or combination of reactions are employed:

-continued

-continued where L is a leaving group, preferably halo, tosylate or mesylate.

The amine is protected with the usual protecting groups such as trityl, t-BOC or hydroborane complex which is removed at the appropriate time.

Introduction of the amine into the bi- or tri-carbocyclic alkane ring may be effected through the azide as follows.

-continued

Treatment of bicyclo[2.2.2]oct-2-ene with m-chloroperoxybenzoic acid to form the epoxide followed by ring opening with sodium azide (18-crown 6) results in the bi- or tri-carbocyclic alkane azide. When the later is reduced with triphenylphosphine or Pd/C the amine is prepared. Reduction may take place at various steps in the synthesis and protecting the amine as necessary.

Where A, B or D are O or S, any base normally employed to deprotonate an alcohol or thiol may be used, such as sodium hydride, sodium hydroxide, triethyl amine, sodium bicarbonate or diisopropylethylamine.

Reaction temperatures are in the range of −78° C. to reflux depending on the reactants involved. (Preferably 0° C. to room temperature). Reaction times vary from about 2 to about 96 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

In the case where A, B or D is SO or $SO_2$, then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating hydrogen peroxide, preferably about 30% aqueous $H_2O_2$.

In certain of the following reaction schemes a metal salt may be used. Any appropriate metal salt such as Li, K, Na, Mg, or the like may be used.

Those compounds where B is —C═O may be prepared by the following reaction sequence, where treatment of the substituted metal salt compound, such as the lithium, sodium potassium or Grignard compound, with an N-alkyl-N-alkoxybenzamide following the procedure of S. Nahm and S. M. Weinreb in Tet. Letters, 22, 3815 (1981) results in the formation of the carbonyl chain, making sure the amine is properly protected which may be removed in the usual manner.

Condensation of a ketone with an appropriate hydroxylamine results in the formation of the oxime, while Wittig condensation of a ketone using $Ph_3 P=CH_2$ results in the methylene compounds; Wittig condensation also may take place at the A or D position of the molecule. This may be carried out using normal Witting reaction conditions. When the appropriate aldehyde or ketone is reacted with a Wittig reagent then condensation results in formation of the double bond. This may then be reduced catalytically by known procedures such as Pd/C or any other suitable hydrogenating condition. The Wittig reagent is prepared by known art recognized procedures such as reaction of triphenylphosphine or diethylphosphone, with a substituted alkyl bromide followed by treatment with a strong organometallic or alkoxide base, such as n-BuLi or NaOH, results in the desired ylide. Of course this Witting condensation may also take place when the Wittig reagent is formed on the quinuclidine position of the molecule which is then condensed with the aldehyde from the Ar III portion.

Halogenation with $Br_2$ in $CCl_4$ on the double bond followed by double dehydration with $NaNH_2$/liq $NH_3$ results in the triple bond compounds.

When A or B is —NR—CO— or —CO—NR— then condensation (while protecting the amine) of an acid halide with the appropriate aniline will give the desired compound such as examples in the following schemes.

Condensation of the metal salt with a substituted phenylisocyanate (while protecting the amine) results in the corresponding amide, as shown above. Reverse condensation will give the corresponding reverse amide.

Condensation of the acid halide with the appropriate aniline will give the desired amide compound.

Condensation of the metal salt with an aldehyde or ketone followed by dehydration results in the appropriate ring addition, as shown below.

Those compounds of the special embodiment may be prepared as follows:

Incorporation by reference for the above reaction steps is as follows:

(a) J. Colonge and R. Vuillemet; *Bull. Soc. Chim. Fr.;* 1961, 2235.D.;

(b) Balderman.and A. Kalir; *Synthesis;* 1978, 24;

(c) K. Takeuchi and M. Yoshida; *J. Org. Chem.;* 1989, 54, 3772.

Reaction of a 1-azidobicyclo[2.2.2]oct-3-one with an aryl lithium followed by reduction of the azide results in the formation of the amino alcohol.

Certain compounds of this invention may have at least one asymmetric carbon atom such as those compounds having different geminal groups or those compounds which contain an asymmetric carbon atom. Further, certain compounds of this invention may exist in their cis or trans configuration such as those compounds where A, B or D is CR=CR. As a result, those compounds of this invention may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chan, et al, *J. Am. Chem. Soc.* 96, 3642, 1974.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds:* Optical Resolution Information Center, Manhattan College, Riverdale, N.Y. Such procedures are useful in the practice of this invention. A further useful reference is *Enantiomers, Racemates and Resolutions:* Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, oxalic, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in *"Protective Groups in Organic Synthesis"* by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Since the compounds of this invention have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the ring involved.

The compounds of the present invention may be prepared by the following representative examples.

EXAMPLE 1

5-[4-(benzoxazol-2-yl)benzyloxy]tricyclo[3.3.1.1$^{3,7}$]decan-2-amine hydrochloride Step A 5-hydroxytricyclo[3.3.1.1$^{3,7}$]decan-2-amine To a mixture of concentrated sulfuric acid (300 ml) and concentrated nitric acid (30 ml) cooled in an ice bath to 10° C. is added tricyclo[3.3.1.1$^{3,7}$]decan-2-amine hydrochloride (20 g; 0.107 mole) in 5 g portions over 10 minutes. This mixture is then stirred for 2 hours with cooling. The reaction mixture is poured over ice and the pH raised to pH 10–11 using 40% NaOH. This mixture is extracted with chloroform, dried over MgSO$_4$ and evaporated to dryness to give 5-hydroxytricyclo[3.3.1.1$^{3,7}$]decan-2-amine as a solid residue (m.p. 267°–270° C.) which is used directly in step B.

Step B N-trityl-5-hydroxytricyclo[3.1.1$^{3,7}$]decan-2-amine 5-hydroxytricyclo[3.3.1.1$^{3,7}$]decan-2-amine (2.0 g; 0.012 mole) is dissolved in 70 ml of dichloromethane with gentle heating. To this is added triethylamine (2.4 g; 0.024 mole) and cooled in an ice bath. To this is added triphenylmethyl chloride (3.34 g; 0.012 mole) in dichloromethane (10 ml) all at once. The reaction is stirred for 10 minutes with ice cooling and then 5 hours at room temperature. The reaction mixture is heated to reflux overnight, cooled, filtered and evaporated to dryness. Purification is accomplished via HPLC (eluting with 20% ethyl acetate/hexane) to obtain N-trityl-5-hydroxytricyclo[3.3.1.1$^{3,7}$]decan-2-amine (m.p. 166°–170° C.) which is used directly in step E.

Step C 4-(benzoxazol-2-yl)benzyl alcohol

To 500 ml THF cooled to −78° C. is added butyl lithium (2 eq.) followed by 4-bromobenzyl alcohol (27.2 g; 145 mmol) slowly over 45 minutes in a solution of THF (100 ml) keeping the temperature below −72° C. After 10 minutes following the final addition of the alcohol is added 2-chlorobenzoxazole (23.3 g; 145 mmol) in 25 ml THF slowly over 45 minutes. The temperature is maintained at −78° C. for 1 hour and then warmed to −40° C. for 15 minutes. The reaction is then quenched with 15 ml of acetic acid and allowed to warm to room temperature, diluted with 800 ml ether, washed 3× with H$_2$O and brine, dried (MgSO$_4$) and concentrated in vacuo to obtain a brown oily solid which is washed with 400 ml petroleum ether and filtered to obtain 4-(benzoxazol-2-yl)benzyl alcohol as a tan solid which is used directly in Step D.

Step D 4-(benzoxazol-2-yl)benzyl bromide

To 4-(benzoxazol-2-yl)benzyl alcohol (20.9 g; 100 mmol) dissolved in CH$_2$Cl$_2$ (330 ml) and cooled to 0°–5° C. is added thionyl bromide (9.2 ml; 120 mmol) and allowed to warm to room temperature after removing the bath. After 1½ hours, 2,6-lutidine (11.6 ml; 100 mmol) is added to the mixture and warmed to 30° C. The reaction mixture is then diluted with CH$_2$Cl$_2$, washed with H$_2$O 1×, 0.2M HCl 1×, NaHCO$_3$ 2×, brine, dried (MgSO$_4$) and concentrated to dryness. The residue is recrystallized from EtOAc to obtain 4-(benzoxazol-2-yl)benzyl bromide as white-orange needles which is used directly in Step E.

Step E N-trityl-5-[4-(benzoxazol-2-yl)benzyloxy]tricyclo[3.3.1.1$^{3,7}$]decan-2-amine To KH (35%; (0.34 g; 0.0029 mole) in THF (8 ml) under N$_2$ and cooled in an ice bath is added N-trityl-5-hydroxytricyclo-[3.3.1.1$^{3,7}$]decan-2-amine (1.0 g; 0.0025 mole) This forms a pale yellow solution and is stirred at room temperature for 1 hour. The reaction mixture is then cooled in ice and 4-(benzoxazol-2-yl)benzyl bromide (0.7 g; 0.0025 mole) is added all at once. The mixture is stirred for ½ hour with ice cooling and then 3½ hours at room temperature then cooled in ice and MeOH is added to quench the KH. The mixture is evaporated to dryness. Purification is accomplished on HPLC eluting with a gradient system staring with 10% and ending with 20% ethyl acetate/hexane to obtain N-trityl-5-[4-(benzoxazol-2-yl)benzyloxy]tricyclo[3.3.1.1$^{3,7}$]decan-2-amine which is used directly in step F.

Step F 5-[4-(benzoxazol-2-yl)benzyloxy]tricyclo[3.3.1.1$^{3,7}$]decan-2-amine hydrochloride A mixture of N-trityl-5-[4-(benzoxazol-2-yl)benzyloxy]tricyclo[3.3.1.1$^{3,7}$]decan-2-amine (200 mg) combined with ethanolic hydrogen chloride (5 ml) is stirred for an hour at room temperature. This is evaporated to dryness and the components separated via flash chromatography (eluting with 10% MeOH/CH$_2$Cl$_2$) to obtain 5-[4-(benzoxazol-2-yl)benzyloxy]tricyclo[3.3.1.1$^{3,7}$]decan-2-amine hydrochloride (m.p. 278°–281° C).

EXAMPLE 2

3-[-(benzoxazol-2-yl)benzyloxy]tricyclo[3.3.1.1$^{3,7}$]decan-1-amine hydrochloride Step A 3-hydroxytricyclo[3.3.1.1$^{3.7}$]decan-1-amine To a mixture of 150 ml of concentrated sulfuric acid and 15 ml of concentrated nitric acid, cooled to 10° C. is added 10 g (0.053 moles) of 1-adamantanamine hydrochloride over 5 minutes. This mixture is stirred in an ice bath for 4 hours. The reaction is then poured over ice and the pH adjusted to pH 10 using 50% NaOH. The product is extracted into chloroform which is dried over MgSO$_4$ and then evaporated to dryness. The residue is recrystallized from ethyl acetate to give 3-hydroxytricyclo[3.3.1.1$^{3,7}$]decan-1-amine (m.p. 260°–264° C.) which is used directly in step B.

Step B N-trityl-3-hydroxytricyclo[3.3.1.1$^{3,7}$]decan-1-amine

To 3-hydroxytricyclo[3.3.1.1$^{3,7}$]decan-1-amine (5 g; 0.03 mole) dissolved in dichloromethane (140 ml) with gentle heating is added triethylamine (6 g; 0.06 mole) and cooled in an ice bath. Triphenylmethyl chloride (8.30 g; 0.03 mole) in CH$_2$Cl$_2$ (10 ml) is added all at once. The reaction is stirred in an ice bath for 10 minutes, warmed to room temperature and then refluxed for 3 hours. The reaction is then filtered and the filtrate evaporated to dryness. The reaction products are separated on HPLC, using 15% ethyl acetate/hexane and the product is then recrystallized from ethyl acetate/pet. ether to give N-trityl-3-hydroxytricyclo-[3.3.1.1$^{3,7}$]decan-1-amine (m.p. 184°–186° C.) which is used directly in step C.

Step C N-trityl-3-[4-(benzoxazol-2-yl)benzyloxy]tricyclo[3.3.1.1$^{3,7}$]decan-1-amine To KH (35%; 0.35 g; 0.003 mole) in THF (8 ml) under N$_2$ and cooled to 0° C. is added N-trityl-3-hydroxytricyclo-[3.3.1.1$^{3,7}$]decan-1 -amine (1 g; 0.0025 mole) of all at once. The reaction is stirred for 5 minutes with ice cooling then at room temperature for an hour, developing into a clear yellow solution. Then 4-(benzoxazol-2-yl)benzyl bromide (0.70 g; 0.0025 mole) is added and the reaction cooled in ice for 10 minutes and stirred at room temperature for 4 hours. Methanol is added to quench any KH, then the reaction is filtered and evaporated to dryness. HPLC is used to purify the product (eluting with 10% ethyl acetate/hexane) to obtain N-trityl-3-[4-(benzoxazol-2-yl)benzyloxy]tricyclo[3.3.1.1$^{3,7}$]decan-1-amine (m.p. 174°–177° C.) which is used directly in step D.

Step D 3-[4-(benzoxazol-2-yl)benzyloxy]tricyclo[3.3.1.1$^{3,7}$]decan-1-amine hydrochloride A mixture of N-trityl-3-[4-(benzoxazol-2-yl)benzyloxy]tricyclo[3.3.1.1$^{3,7}$]decan-1-amine (0.48 g; 0.0008 mole) is combined with ethanolic HCl (10 ml) and stirred for 1 hour at room temperature. A white precipitate develops and is filtered off. The crude product is purified on a flash column, using 10% MeOH/CH$_2$Cl$_2$ as eluant to obtain 3-[-(benzoxazol-2-yl)benzyloxy]tricyclo[3.3.1.1$^{3,7}$]decan-1-amine hydrochloride (m.p. 309°–310° C.).

EXAMPLE 3

1-[4-(benzoxazol-2-yl)benzyloxytricyclo[3.3.1.1$^{3,7}$]decan-2-amine hydrochloride Step A  N-trityl-1-hydroxytricyclo[3.3.1.1$^{3,7}$]decan-2-amine To 1-hydroxytricyclo[3.3.1.1$^{3,7}$]decan-2-amine (0.47 g; 0.0028 mole), [prepared via a procedure of W. V. Curran and R. B. Angier, *J. of Org. Chem.*, 34(11), 3668–70 (1969)] in dichloromethane (45 ml) is added triphenylmethyl chloride (0.78 g; 0.0028 mole) in dichloromethane (5 ml). This mixture is refluxed for 7 hours and then more triphenylmethyl chloride (0.35 g) is added and the reaction refluxed overnight. The reaction is stripped to dryness and the products separated via flash chromatography (eluted with 25% ethyl acetate/hexane) to obtain N-trityl-1-hydroxytricyclo[3.3.1.1$^{3,7}$]decan-2-amine which is used directly in step B.

Step B  N-trityl-1-[4-(benzoxazol-2-yl)benzyloxy]tricyclo[3.3.1.1$^{3,7}$]decan-2-amine To KH (35%; 0.43 g; 0.0038 mole) in THF (10 ml) under N2 and cooled in ice is added N-trityl-1-hydroxytricyclo[3.3.1.1$^{3,7}$]decan-2-amine (1.3 g; 0.0032 mole) and this mixture is stirred in an ice bath for 5 minutes and then at room temperature for an hour. To this mixture is added 4-(benzoxazol-2-yl)benzyl bromide all at once and an immediate yellow suspension develops. The reaction is stirred at room temperature for 4 hours, filtered and the filtrate stripped to dryness to give a solid residue. The components are separated on HPLC, eluting with 8% ethyl acetate/hexane to obtain N-trityl-1-[4-(benzoxazol-2-yl)benzyloxy]tricyclo[3.3.1.1$^{3,7}$]decan-2-amine (m.p. 208°–210° C.) which is used directly in step C.

Step C 1-[4-(benzoxazol-2-yl)benzyloxy]tricyclo[3.3.1.1$^{3,7}$]decan-2-amine hydrochloride N-trityl-1-[4-(benzoxazol-2-yl)benzyloxy]tricyclo[3.3.1.1$^{3,7}$]-decan-2-amine (0.88 g; 0.0014 mole) is combined with ethanolic HCl (20 ml). After 2 hours, TLC indicates the reaction is complete. The reaction mixture is evaporated to dryness and purified on a flash column, using 10% MeOH/CH$_2$Cl$_2$ to obtain 1-[4-(benzoxazol-2-yl)benzyloxy]-tricyclo[3.3.1.1$^{3,7}$]-decan-2-amine hydrochloride (m.p. 291°–293° C.).

EXAMPLE 4

N,N-dimethyl-3-[4-(benzoxazol-2-yl)benzyloxy]tricyclo[3.3.1.1$^{3,7}$]decan-1-amine hydrochloride Step A N,N-dimethyl-3-hydroxytricyclo[3.3.1.1$^{3,7}$]decan-1-amine To a mixture of 3-hydroxytricyclo[3.3.1.1$^{3,7}$]decan-1-amine (1.5 g; 0.009 mole) and formic acid (96%; 2.1 g; 0.046 mole) is added formaldehyde (37%; 1.62 g; 0.054 mole) and then heated in an oil bath at 60° C. for 24 hrs. The reaction mixture is cooled and to this is added conc. HCl (0.75 ml), then evaporated to dryness. The residue is then dissolved in water and basified (to pH 14) via 30% KOH, which forms a crystalline product upon standing. The product is recrystallized from ether/pet. ether to give N,N-dimethyl-3-hydroxytricyclo-[3.3.1.1$^{3,7}$]decan-1-amine (m.p. 60°–64° C.) which is used directly in Step B.

Step B borane N,N-dimethyl-3-hydroxytricyclo[3.3.1.1$^{3,7}$]decan-1-amine complex To N,N-dimethyl-3-hydroxytricyclo-[3.3.1.1$^{3,7}$]decan-1-amine (1.3 g; 0.0067 mole) dissolved in THF, under N$_2$ and chilled in ice, is added borane-THF (14 ml; 0.014 mole) over 5 min. The ice bath is removed after an additional 5 min. and stirred at room temperature for 3 hrs. To this mixture is added ether (100 ml), washed with saturated NaHCO$_3$ and evaporated to dryness to give borane N,N-dimethyl-3-hydroxytricyclo[3.3.1.1$^{3,7}$]decan-1-amine complex which is used directly in Step C.

Step C N,N dimethyl 3-[4-(benzoxazol-2-yl)benzyloxy]tricyclo[3.3.1.1$^{3,7}$]decan-1-amine hydrochloride To KH (35%; 0.55 g; 0.0058 mole) in THF (5 ml), under N$_2$ and cooled to 0° C., is added borane N,N-dimethyl-3-hydroxytricyclo[3.3.1.1$^{3,7}$]decan-1-amine complex (1 g; 0.0048 mole), which is partially solubilized in THF (10 ml) containing ether (5 ml). This white suspension is stirred for an hour at room temperature. To this mixture is then added 4-(benzoxazol-2-yl)benzyl bromide (1.38 g; 0.0048 mole) all at once. This is stirred for 8 hrs. at room temperature, then more KH (0.25g) is added. The reaction mixture becomes orange in color and more viscous. After another 2 hrs. at room temperature, the reaction mixture is chilled, MeOH is added to quench any KH and then evaporated to dryness. The reaction products are separated via flash chromatography (eluted with 25% ethyl acetate/hexane). The product obtained is added to acetone and acidified with ethanolic HCl to give N, N dimethyl 3-[4-(benzoxazol-2-yl)benzyloxy]tricyclo-[3.3.1.1$^{3,7}$]decan-1-amine hydrochloride (m.p. 278°–280° C.).

EXAMPLE 5

2-aminomethyl-5-[4-(benzoxazol-2-yl)benzyloxy]tricyclo[3.3.1.1$^{3,7}$]decan-2-ol hydrochloride Step A 5-hydroxytricyclo[3.3.1.1$^{3,7}$]decan-2-one To a mixture of H$_2$SO$_4$ (96%; 150 ml) and HNO$_3$ (70%; 15 ml), cooled to 0° C. is added tricyclo[3.3.1.1$^{3,7}$]decan-2-one (10 g; 0.067 mole) and the mixture stirred at room temperature for 5 hrs. The reaction mixture is then poured over ice, basified to pH 8 using 50% NaOH, extracted into ether, dried over MgSO$_4$ and evaporated to dryness. The resultant product is recrystallized from carbon tetrachloride to obtain 5-hydroxytricyclo[3.3.1.1$^{3,7}$]decan-2-one [(m. p. 314° C. (dec.)] which is used directly in step B.

Step B 5-[4-(benzoxazol-2-yl)benzyloxy]tricyclo[3.3.1.1$^{3,7}$]decan-2-one

To KH (35%; 1.38 g; 0.012 mole) in THF (20 ml) under N$_2$ and cooled to 0° C. is added 5-hydroxytricyclo[3.3.1.1$^{3,7}$]decan-2-one (2 g; 0.012 mole) all at once. The reaction mixture is stirred for 5 min. in an ice bath and 1 hr. at room temperature. To the reaction mixture is then added 4-(benzoxazol-2-yl)benzyl bromide (3.4 g; 0.012 mole) dissolved in THF (60 ml) at a fast drip rate. A bright yellow mixture forms and the mixture is stirred overnight at room temperature. The mixture is next cooled in an ice bath, MeOH added to quench any KH and filtered. The filtercake is washed with THF and evaporated to dryness. The product is purified using a gradient flash chromatography (eluting with 10%–25% ethyl acetate/hexane) to obtain 5-[4-(benzoxazol-2-yl)benzyloxy]tricyclo[3.3.1.1$^{3,7}$]decan-2-one (m.p. 159°–160° C.) which is used directly in Step C.

Step C 2-trimethylsilyloxy-2-cyano-5-[4-(benzoxazol-2-yl)benzyloxy]tricyclo[3.3.1.1$^{3,7}$]decane To a solution of 5-[4-(benzoxazol-2-yl)benzyloxy]tricyclo-[3.3.1.1$^{3,7}$]decan-2-one (1.05 g; 0.0028 mole) in dichloromethane (12 ml) under N$_2$ is added zinc iodide (7 mg) followed by trimethylsilylcyanide (0.45 ml; 0.0034 mole) added by syringe over 1 min. The reaction mixture was stirred at room temperature overnight and then the mixture is evaporated to dryness to give 2-trimethylsilyloxy-2-cyano-5-[4-(benzoxazol-2-yl)benzyloxy]tricyclo[3.3.1.1$^{3,7}$]decane which is used directly in Step D.

Step D 2-aminomethyl-5-[4-(benzoxazol-2-yl)benzyloxy]tricyclo[3.3.1.1$^{3,7}$]decan-2-ol hydrochloride To a suspension of lithium alumium hydride (0.044 g; 0.0012 mole) in THF (10 ml) under N$_2$ is added cyanohydrin silyl ether (0.5 g; 0.0011 mole) in THF (20 ml) and the mixture is stirred at room temperature for 4 hrs. The reaction mixture is then cooled to 0° C. and water (0.1 ml) added dropwise followed by KOH (30%; 0.1 ml) and water (0.2 ml). To this mixture is then added ether (30 ml), the layers are separated, the organic layer is dried over MgSO$_4$ and evaporated to dryness. To the residue is added dichloromethane followed by ethanolic HCl which gives 2-aminomethyl-5-[4-(benzoxazol-2yl)benzyloxy]tricyclo[3.3.1.1$^{3,7}$]-decan-2-ol hydrochloride [m.p. 291 ° C. (dec.)].

EXAMPLE 6

When 4-(benzoxazol-2-yl)benzyl bromide in Example 1, Step E, Example 2, Step C, Example 3, Step B, Example 4, Step C and Example 5, Step B is replaced by the following compounds of Table I below, then the corresponding products are prepared.

Table I 4-biphenylmethyl bromide 4-styrylbenzyl bromide 4-(cyclohexen-1-yl)benzyl bromide 4-phenylmethoxybenzyl bromide 3,4-dichlorophenoxybenzyl bromide 4-chlorobenzoylbenzyl bromide 4-(2-phenylethyl)benzyl bromide 2-benzylbenzyl bromide 3-benzyloxybenzyl bromide 2-phenethylbenzyl bromide 4-(2,5-dimethylstyryl)benzyl bromide 4-(4-fluorostyryl)benzyl bromide 4-phenoxybenzyl bromide 4-((1-benzoyl-1-methyl)ethyl)benzyl bromide 4-benzoylbenzyl bromide N-methylbenzamidobenzyl bromide 4-phenylethynylbenzyl bromide 4-(1-(4-chlorophenyl)ethenyl)benzyl bromide 4-(1-(2-chlorophenyl)ethenyl)benzyl bromide 4-(4-methylphenylsulfonyl)benzyl bromide 3-benzoylbenzyl bromide 4-(benzoxazol-2-yl)benzyl bromide 4-(benzothiazol-2-yl)benzyl bromide 4-(2-naphthoyl)benzyl bromide 4-(2-quinolinyl)benzyl bromide 4-(6-quinolinyl)benzyl bromide Various tests have been carried out to show the ability of the compounds of the present invention to exhibit pharmacological responses that can be correlated with activity in humans. These tests involve such factors as the effect of the compounds of Formula I to inhibit squalene synthesis. It has been found that compounds within the scope of this invention when tested using the following procedures show a marked activity for the inhibition of squalene synthase and hence are believed to be useful in the treatment of cholesterol-related disorders.

Squalene Synthase Inhibition Assay

The squalene synthase assay used is a modification of the procedures described by Popjak (1969) and Poulter et al. (1989):

Popjak, G. Enzymes of sterol biosynthesis in liver and intermediates of sterol biosynthesis. *Meth. Enzymol.* 15: 393–454, 1969.

Poulter, C. D., Capson, T. L., Thompson, M. D. and Bard R. S. Squalene synthase. Inhibition by ammonium analogues of carbocationic intermediates in the conversion of presqualene diphosphate to squalene. *J. Am. Chem. Soc.* 111: 3734–3739, 1989.

I. Animal Source and Tissue Preparation:

Four male Sprague-Dawley rats weighing 100–120 gms are fed a low cholesterol rodent diet (#5012) obtained from Purina Mills, Inc. in Richmond, Ind.; and housed under reverse-light. Water is given ad lib. Rats are lightly anesthetized with ether and then decapitated. Livers are removed and enzymes are separated by the method described below.

II. Materials:

Chemicals:

All Chemicals are "A.C.S." in purity or better unless noted;

AquaSol®-2 scintillation fluid (NEF-952) (Du Pont/NEN Research Products, Boston, Mass.);

Anhydrous $MgCl_2$ (M-8266), β-NADPH tetrasodium salt, reduced form (N-1630), Bovine serum albumin (A-6003), Cholesterol (C-8503);

Squalene (S-3626), (Sigma Chemical Co., St. Louis, Mo.);

Bio-Rad protein assay dye concentrate (Bio-Rad Laboratories, Richmond, Calif.);

Denatured ethanol, DMSO, HCl (1N), KOH, methanol, NaOH (0.1N, 1N), petroleum ether (M-280 grade), potassium phosphate dibasic, 2-propanol (Fisher Scientific, Pittsburgh, Pa.);

Zero grade nitrogen gas mixture (certified analysis) (Woodland Oxygen & Supply Co., Philadelphia, Pa.).

Radiochemicals:

[1-$^3$H(N)]-FPP, triammonium salt (NET-1042), (Du Pont/NEN, Boston, Mass.);

[4,8,12,13,17,21-$^3$H]-Squalene (NET-645) (Du Pont/NEN);

Non-radiolabeled FPP is prepared in-house. The solid FPP is aliquoted and stored at −80° C. FPP is dissolved in 70% ethanol/30% 0.25M $NH_4HCO_3$ at the concentration of 10 mM and the solution is aliquoted (200 µl each) and stored at −80° C.

III. Preparation of Assay Substances:

A) Test Solutions:

Test solutions are prepared fresh in 100% DMSO or $H_2O$. Subsequent dilutions are made in the same solvent. Compounds are tested initially at 1 or 10 µM (final concentrations).

B) Assay Buffer:

Potassium Phosphate (50 mM, 8.71 g/l) pH 7.5 stock buffer is prepared and stored at 4° C. until use. Anhydrous $MgCl_2$ is added to the phosphate buffer on the day of assay for a final concentration of 10 mM (95 mg/100 ml). The buffer is flushed with $N_2$ before use.

C) Substrate:

Non-radiolabeled FPP is diluted to 50 µM (100 µl 10 mM cold FPP +19.9 ml phosphate buffer). Then, 14 µl (20×10$^6$ dpm) of $^3$H-FPP (0.5 mCi/ml, 0.011 mg/ml) is added. 200 µl of this mixture is added per assay tube for a final reaction concentration of 10 µM FPP (~200,000 dpm/assay tube).

D) β-NADPH Solution:

37.5 mg of β-NADPH is added to 9 ml assay buffer for a 5 mM concentration of β-NADPH. The mixture is vortexed and 100 µl of this solution is added to each tube for a final assay concentration of 0.5 mM β-NADPH.

E) KOH in Ethanol:

75 gm of KOH is dissolved in 500 ml of denatured ethanol for a 15% solution and stored at 0° C. until use. 1 ml of this solution is added per tube to terminate the reaction.

IV. Experimental Procedure:

A) Enzyme Preparation:

Immediately following decapitation, livers are removed one at a time from four rats. The livers are combined and weighed in a tared beaker. Assay buffer is added equal to three times the liver weight. The liver is first homogenized with a blender for thirty seconds, and then by a motor driven Teflon pestle at a speed of 2.5. During homogenization, the liver is kept on ice. When the liver is fully homogenized, the homogenate is centrifuged at 10,000 g for 30 min. at 4° C. in 50 ml capacity centrifuge tubes. The mitochondrial pellet is discarded and the supernatant is filtered through a layer of gauze moistened with a little buffer. This supernatant is recentrifuged at 105,000 g for one hour at 0° C. in an ultracentrifuge in 25 ml capacity ultracentrifuge tubes.

Following centrifugation, the supernatant is removed and discarded. The sediment pellet consists of 2 layers: a transparent inner layer of glycogen, surrounded by an opaque brown layer of microsomes. The brown outer microsomal layer is carefully removed with a spatula and placed in a beaker on ice. Assay buffer is added in an amount equal to one half the original homogenate volume, and this mixture is poured into ultracentrifuge tubes. These tubes are recentrifuged at 105,000 g for 1 hour at 4° C.

After this centrifugation is complete, the supernatant is again removed and discarded. Fresh assay buffer is added to the combined pellets to achieve a volume equal to one tenth of the original homogenate volume. The microsomal fraction is then rehomogenized on a motor driven Teflon pestle at a speed of 2.5 to partially solubilize and make a uniform suspension of the microsomes. The enzyme (~20 ml, ~40 mg protein/ml) is aliquoted (200 µl) into eppendorf plastic tubes, capped and stored at −80° C. until use.

B) Assay Procedure

To begin the assay, 20 µl of the compound of this invention or vehicle solution is added to each 16×150 screw-cap culture tube on ice. Then 580 µl of $N_2$ flushed assay buffer is pipetted into each tube. 100 µl of cofactor is next added to each tube, followed by 100 µl of a dilution of microsomal enzyme (approximately 80 ug protein). The tubes are preincubated for 10 minutes at 37° C., and 200 µl of the $^3$H-FPP (200,000 dpm, 10 µM final conc.) is added to each tube at two second intervals. The tubes are then incubated for exactly 10 minutes, shaking at 150 oscillations per minute. After the 10 minute incubation, the reaction is stopped by the addition of 1 ml of 15% KOH in ethanol, and the tubes are incubated for 30 minutes in a 65° C. water bath for saponification of lipids and solubilization of proteins. The tubes are cooled on ice for five minutes. The samples are next extracted with 5 ml of petroleum ether by shaking for 10 minutes at low speed on a metabolic shaker. Each lower aqueous layer is frozen in a dry ice/alcohol bath (2-propanol/methanol, 1:1), and each organic layer is poured into another set of 16×150 screw-top culture tubes containing 2 ml of deionized water. Each ether layer is washed by vortexing each tube for 5 seconds. The aqueous layers are again frozen in the dry ice/alcohol bath, and the ether is poured into scintillation vials. 10 ml of AquaSol® is next added to each vial, and the vials are counted for 5 minutes in a scintillation counter. Percent inhibitions are calculated from the counts obtained.

V. Statistical Considerations

The samples are counted as dpm using a Beckman Scintillation counter (Model LS-9000). Percent inhibition is calculated using a Lotus 1-2-3 program. The $IC_{50}$ values are calculated using a linear regression program of Tallarida and Murray (1987). Tallarida, R. J. and Murray, R. B. Manual of pharmacologic calculations with computer programs. Springer-Verlag, 1987.

The following in vivo assays are used to determine the effectiveness of compounds of this invention to inhibit squalene synthase.

In Vivo Rat Method:

Forty male Sprague-Dawley rats weighing 80–90 gms are fed a low cholesterol rodent meal diet (#5012) obtained from Purina Mills, Inc. in Richmond, Ind.; and housed under reversed-light. Water is given ad lib. After a week of housing, the rats are fed cholestyramine (2% in diet) for the next 2 days. One day after the cholestyramine treatment, a compound is given three times to 4 rats (30 mg/kg, in 10 ml 0.5% methylcellulose/Kg, p.o.) at 8 a.m., 5 p.m. and 8 a.m. the following day. Four hours after the last dose, the rat is decapitated and blood and the liver are collected. Serum is separated and analyzed for cholesterol by an assay kit supplied by Sigma Chemical Co., St. Louis, Mo. Sterols in the serum and the liver are also analyzed by HPLC analysis. The liver cholesterol level is determined by quantitating against cholesterol as a standard by HPLC. Results are determined as the change in the liver and serum cholesterol compared to respective vehicle treated control values.

Mouse in vivo assay for cholesterol-lowering effect:

Balb-c mice weighing 20–25 gms are used for this study. Mice are fed a meal diet (RP#5012) containing 2% cholestyramine. Test compound is dissolved/suspended in 0.5% methyl cellulose and given to mice at 50 mg/kg, b.i.d. (n=8). Blood is collected from the tail on days 0 and 7 and from inf. vena cava on day 14. Body weights and the food consumption are monitored weekly. Serum cholesterol is determined by an enzyme assay kit (Sigma Chemical Co.). Serum and the liver are analyzed by HPLC for various sterols. Results are determined as % change from the vehicle treated controls.

HPLC Procedure

Sample preparation:

In 16×125 mm screw cap glass tubes, is added 0.5 ml serum or plasma or liver slices suspension (0.11 gm/ml buffer). To this is then added 1 ml of KOH/ethanol (15%). The glass tubes are incubated at 80° C. for 2 hours while shaking. After saponification, 10 ml petroleum ether is added to each tube and then capped. The tubes are shaken for 30 min. then frozen at −80° C. and the ether removed to 16×150 mm screw top glass tubes. Water (2 ml) is added and again the tubes are shaken for 10 minutes. After freezing, the ether is transferred into 16×125 mm glass culture tubes. The ether is evaporated under $N_2$. HPLC grade ethanol (0.5 ml) is added to the tubes, capped and shaken for 30 min. to dissolve all lipids, The ethanol is filtered using a syringe filter (pore size:0.45 uM, Spartan-13, Schleicher & Schuell) and 50 ul of this solution is injected into HPLC.

HPLC specifications:

Column: Partisil 10 ODS-3, C-18 reversed phase, 25 cm length at 25° C.
[Whatman Cat#4228-001]

Pump: Waters 6000A, Isocratic system

Solvent: Acetonitrile:water:: 95:5; 2 ml/min

Run Time: 33 min 50 ul injection by Autosampler WISP 710B, Waters/Millipore

Wavelength: 210 nm, Applied Biosystems 757 Absorbance detector

Integrator: Hewlett Packard 3396 Series II.

Typical Retention Times:

Squalene dioxide—7.5 min

Squalene oxide—14 min 7-dehydro Chol.—16 min

Cholesterol—23 min

Squalene—30 min

Compounds within the scope of Formula I have been tested by the foregoing assay procedures and exhibit marked squalene synthase inhibition activity and are useful as hypocholesterolemic or hypolipidemic agents by virtue of their ability to inhibit the biosynthesis of cholesterol. Having such ability, the compounds are incorporated into pharmaceutically acceptable carriers and administered to a patient in need of such cholesterol biosynthesis inhibition. These pharmaceutical formulations contain at least one compound according to this invention.

Treatment with a combination of an HMG-CoA reductase inhibitor and a squalene synthase inhibitor would have a synergistic effect on inhibiting cholesterol biosynthesis. Inhibiting the squalene synthase enzyme and the HMG-CoA reductase enzyme at the same time would most closely resemble the physiological conditions of cholesterol homeostasis. A squalene synthase inhibitor could keep cellular concentrations of farnesyl diphosphate high enough for the synthesis of the small amounts of dolichol, ubiquinone, and the farnesylated proteins required by the cell. This would maintain some feedback regulation of the HMG-CoA reductase enzyme and allow smaller amounts of the HMG-CoA reductase inhibitor to be used.

Other combinations with a squalene synthase inhibitor which could have an additive or synergistic effect for controlling undesirable cholesterol levels in the body include niacin, antihyperlipoproteinemic agents such as gemfibrozil, cholesterol absorption inhibitors, bile acid sequestrants, antioxidants and lipoxygenase inhibitors.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium-chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from about 0.1 to about 100 mg/kg/dy, and preferably from about 10 mg to about 1000 mg day, or from about 0.1 mg to about 50 mg/kg of body weight per day and preferably from about 0.1 to about 20 mg/kg of body weight per day and may be administered in several different dosage units. Higher dosages on the order of about 2× to about 4× are required for oral administration.

We claim:

1. A compound of the formula:

where:

A is O or NH;

R' is hydrogen or lower alkyl;

R" is hydrogen or lower alkyl;

$R_1$ and $R_2$ are hydrogen or lower alkyl;

$R_3$ is hydrogen or loweralkyl;

a is 0–3;

m and n are independently 0–2 or a pharmaceutically acceptable salt thereof.

2. A compound according to claim 1 where:

A is NH;

R' is hydrogen;

R" is hydrogen;

$R_1$ and $R_2$ are independently hydrogen or lower alkyl;

$R_3$ is hydrogen or lower alkyl;

a is 2–3;

m and n are independently 0–2.

3. A compound according to claim 1 of the formula:

where:

A is O;

R' and R" are hydrogen or lower alkyl;

$R_1$ and $R_2$ are independently hydrogen or lower alkyl;

$R_3$ is hydrogen or lower alkyl;

a is 0; and m and n are independently 0–2.

4. A compound according to claim 3 which is 5-[4-(phenyl)benzyloxy]tricyclo[3.3.1.1$^{3,7}$]decan-2-amine or a pharmaceutically acceptable salt thereof.

5. A compound according to claim 3 which is 3-[4-(phenyl)benzyloxy]tricyclo[3.3.1.1$^{3,7}$]decan-1-amine or a pharmaceutically acceptable salt thereof.

6. A compound according to claim 3 which is 1-[4-(phenyl)benzyloxy]tricyclo[3.3.1.1$^{3,7}$]decan-2-amine or a pharmaceutically acceptable salt thereof.

7. A method of lowering or maintaining reduced cholesterol levels in a patient requiring such treatment which comprises administering to such patient a squalene synthase inhibitor effective amount of a compound of the formula according to claim 1.

8. A method for inhibiting cholesterol biosynthesis which comprises administering to a patient in need of such inhibition a squalene synthase inhibiting effective amount of a compound according to claim 1.

9. A method according to claim 8 where the patient is in need of a hypocholesterolemic or hypolipidemic agent.

10. A method according to claim 9 for treating atherosclerosis.

11. A pharmaceutical composition comprising a squalene synthase inhibitor effective amount of a compound according to claim 1 in admixture with a pharmaceutical carrier.

12. A pharmaceutical composition according to claim 11 which further includes an HMG CoA reductase inhibitor.

* * * * *